US012564716B2

(12) United States Patent
Schallhorn et al.

(10) Patent No.: US 12,564,716 B2
(45) Date of Patent: Mar. 3, 2026

(54) TONIC EYELID CLOSURE AND BLINK PACING DEVICE AND METHOD

(71) Applicants: The United States Government as represented by the Department of Veterans Affairs, Washington, DC (US); The Regents of the University of California, Oakland, CA (US)

(72) Inventors: Julie Schallhorn, San Francisco, CA (US); Nailyn Rasool, San Francisco, CA (US)

(73) Assignees: THE UNITED STATES GOVERNMENT AS REPRESENTED BY THE DEPARTMENT OF VETERANS AFFAIRS, Washington, DC (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 321 days.

(21) Appl. No.: 18/212,774

(22) Filed: Jun. 22, 2023

(65) Prior Publication Data

US 2023/0414943 A1     Dec. 28, 2023

Related U.S. Application Data

(60) Provisional application No. 63/354,267, filed on Jun. 22, 2022.

(51) Int. Cl.
*A61N 1/36* (2006.01)
*A61N 1/05* (2006.01)
*A61N 1/04* (2006.01)

(52) U.S. Cl.
CPC ....... *A61N 1/3606* (2013.01); *A61N 1/36034* (2017.08); *A61N 1/36157* (2013.01); *A61N*

*1/36171* (2013.01); *A61N 1/0456* (2013.01); *A61N 1/0492* (2013.01); *A61N 1/0551* (2013.01)

(58) Field of Classification Search
CPC .............. A61N 1/3606; A61N 1/36034; A61N 1/36157
USPC .......................................................... 607/59
See application file for complete search history.

(56) References Cited

U.S. PATENT DOCUMENTS

2013/0158612 A1* 6/2013 Lindenthaler ...... A61N 1/36067
607/3

FOREIGN PATENT DOCUMENTS

WO     WO-2020035852 A2 * 2/2020 ......... A61N 1/36031

* cited by examiner

*Primary Examiner* — Nadia A Mahmood
(74) *Attorney, Agent, or Firm* — Ballard Spahr LLP

(57) ABSTRACT

A device for stimulating left and right eyelid closure of a patient. A first pair of electrodes is configured to be attached in spaced apart relation to one another proximate to a left facial nerve of the patient for activating closure of the left eyelid. A second pair of electrodes is configured to be attached in spaced apart relation to one another proximate to a right facial nerve of the patient for activating closure of the right eyelid. A controller in communication with the first and second pairs of electrodes is configured to provide electrical signals to the first and second pairs of electrodes for stimulating closure of the left and right eyelids. A power supply in communication with the controller is configured to supply electrical power to the controller and the first and second pairs of electrodes.

19 Claims, 3 Drawing Sheets

TONIC EYELID CLOSURE AND BLINK PACING DEVICE AND METHOD

CROSS REFERENCE TO RELATED APPLICATIONS

This application is based upon and claims priority to U.S. Provisional Application No. 63/354,267, filed Jun. 22, 2022 and hereby incorporated by reference herein in its entirety.

FIELD OF THE INVENTION

This invention concerns devices for producing extended (tonic) eyelid closure in a patient as well as controlling eye blink rate and degree of eyelid closure.

BACKGROUND

Eyelid closure is protective to the corneal epithelium and necessary to allow regeneration and healing of the ocular surface. Good closure is especially important when the surface of the eye has become compromised and has lost sensation, a process known as neurotrophic keratitis. This is a potentially blinding condition where the epithelium repeatedly breaks down, leaving the eye susceptible to infection and scaring with subsequent loss of vision. In cases of neurotrophic keratitis, physicians often have to resort to sewing the eyelids shut to maintain lid closure to protect the eye, a procedure known as a tarsorrhaphy. This is very effective but cosmetically disfiguring, and even with reversal can result in damage to the eyelids. Alternatives to this procedure, such as taping the eyelids shut, or chemoparalysis of the levator palpebrae muscle have numerous disadvantages as well. Neither alternative ensures adequate eyelid closure.

Control of blink rate is another potentially serious dysfunction. The normal blink rate varies by gender and age, but is generally within the range of 10-20 blinks per minute. With normal aging, the blink rate decreases, as does the blink amplitude. Some of the many neurological conditions that result in a marked decrease in the blink rate and blink amplitude include Parkinson's disease and Progressive Supranuclear Palsy. Blink rate or blink amplitude reductions can result in failure to replenish and the tear film over the ocular surface, which can lead to dry eye, ocular surface breakdown, and reduced visual acuity.

There is clearly an opportunity to address and alleviate blink and tonic eyelid dysfunctions.

SUMMARY

An example device for stimulating left and right eyelid closure of a patient is disclosed. The device comprises a first pair of electrodes configured to be attached in spaced apart relation to one another proximate to a left facial nerve of the patient for activating closure of the left eyelid. A second pair of electrodes is configured to be attached in spaced apart relation to one another proximate to a right facial nerve of the patient for activating closure of the right eyelid. A controller in communication with the first and second pairs of electrodes is configured to provide electrical signals to the first and second pairs of electrodes for stimulating closure of the left and right eyelids. A power supply in communication with the controller is configured to supply electrical power to the controller and the first and second pairs of electrodes.

In an example embodiment, the controller is configured to provide the electrical signals to the first and second electrode pairs stimulating tonic eyelid closure of the right and left eyelids.

In an example embodiment, the controller is configured provide the electrical signals to the first and second electrode pairs stimulating blinking of the right and left eyelids.

In an example embodiment, the controller is configured to provide the electrical signals to the first and second electrode pairs controlling a rate of blink of the right and left eyelids.

In an example embodiment, the controller is configured to provide the electrical signals to the first and second electrode pairs controlling a degree of closure of the right and left eyelids.

In an example embodiment, the controller comprises a driver configured to produce the electrical signals comprising a periodic waveform from 0.001 Hz to 1 Hz.

In an example embodiment, the periodic waveform comprises a square wave.

In an example embodiment, the controller comprises a driver configured to produce the electrical signals comprising a current from 5 mA Hz to 100 mA.

In an example embodiment, the first and second electrode pairs comprise first and second pairs of electrode pads configured to be respectively attached transcutaneously on left and right temples of the patient.

In an example embodiment, for each of the pair of electrode pads, one of the electrode pads, configured to have a positive electrical charge, is configured to be positioned on one side of the facial nerve, and another one of the electrode pads, configured to have a negative electrical charge, is configured to be positioned on an opposite side of the facial nerve.

In an example embodiment, the controller is configured to provide the electrical signals to stimulate closure of one of the eyelids at a time.

In an example embodiment, the controller is configured to provide the electrical signals to stimulate closure of both of the eyelids at a time.

In an example embodiment, the device further comprises a first neural blockade electrode configured to be transcutaneously attached to the left eyelid, and a second neural blockade electrode configured to be transcutaneously attached to the right eyelid. The controller is configured to provide blocking electrical signals to the first and second neural blockade electrodes to block left and right branches of the patient's oculomotor nerves to facilitate closure of the eyelids.

In an example embodiment, the blocking electrical signals comprise a kilohertz frequency alternating electrical current.

In an example embodiment, the device further comprises a first neural blockade electrode configured to be subcutaneously implanted around a superior branch of a left oculomotor nerve of the patient, and a second neural blockade electrode configured to be subcutaneously implanted around a superior branch of a right oculomotor nerve of the patient. The controller is configured to provide blocking electrical signals to the first and second neural blockade electrodes to block left and right branches of the patient's oculomotor nerves to facilitate closure of the eyelids.

In an example embodiment, the blocking electrical signals comprise a kilohertz frequency alternating electrical current.

A device for stimulating left and right eyelid closure of a patient is disclosed. The device comprises a first bipolar electrode configured to be subcutaneously implanted proximate to a left facial nerve of the patient for activating closure of the left eyelid. A second bipolar electrode is configured to be subcutaneously implanted proximate to a right facial nerve of the patient for activating closure of the right eyelid. A controller is in communication with the first and second bipolar electrodes. The controller is configured to provide electrical signals to the first and second bipolar electrodes for stimulating closure of the left and right eyelids. A power supply is in communication with the controller. The power supply is configured to supply electrical power to the controller and the first and second bipolar electrodes.

In an example embodiment, the controller is configured to provide the electrical signals to the first and second bipolar electrodes stimulating tonic eyelid closure of the right and left eyelids.

In an example embodiment, the controller is configured provide the electrical signals to the first and second bipolar electrodes stimulating blinking of the right and left eyelids.

In an example embodiment, the controller is configured to provide the electrical signals to the first and second bipolar electrodes controlling a rate of blink of the right and left eyelids.

In an example embodiment, the controller is configured to provide the electrical signals to the first and second bipolar electrodes controlling a degree of closure of the right and left eyelids.

In an example embodiment, the controller comprises a driver configured to produce the electrical signals comprising a periodic waveform from 0.001 Hz to 1 Hz.

In an example embodiment, the periodic waveform comprises a square wave.

In an example embodiment, the controller comprises a driver configured to produce the electrical signals comprising a current from 5 mA Hz to 100 mA.

In an example embodiment, the first and second bipolar electrodes are configured to be implanted along respective frontal branches of the left and right facial nerves.

In an example embodiment, the controller is configured to be subcutaneously implanted within the patient.

In an example embodiment, the power supply is configured to be subcutaneously implanted within the patient.

In an example embodiment, the controller is configured to provide the electrical signals to stimulate closure of one of the eyelids at a time.

In an example embodiment, the controller is configured to provide the electrical signals to stimulate closure of both of the eyelids at a time.

In an example embodiment, the device further comprises a first neural blockade electrode configured to be attached to the left eyelid, and a second neural blockade electrode configured to be attached to the right eyelid. The controller is configured to provide blocking electrical signals to the first and second neural blockade electrodes to block left and right branches of the patient's oculomotor nerves to facilitate closure of the eyelids.

In an example embodiment, the blocking electrical signals comprise a kilohertz frequency alternating electrical current.

In an example embodiment, the device further comprises a first neural blockade electrode configured to be subcutaneously implanted around a superior branch of a left oculomotor nerve of the patient, and a second neural blockade electrode configured to be subcutaneously implanted around a superior branch of a right oculomotor nerve of the patient. The controller is configured to provide blocking electrical signals to the first and second neural blockade electrodes to block left and right branches of the patient's oculomotor nerves to facilitate closure of the eyelids.

In an example embodiment, the blocking electrical signals comprise a kilohertz frequency alternating electrical current.

DETAILED DESCRIPTION

Figure 1:
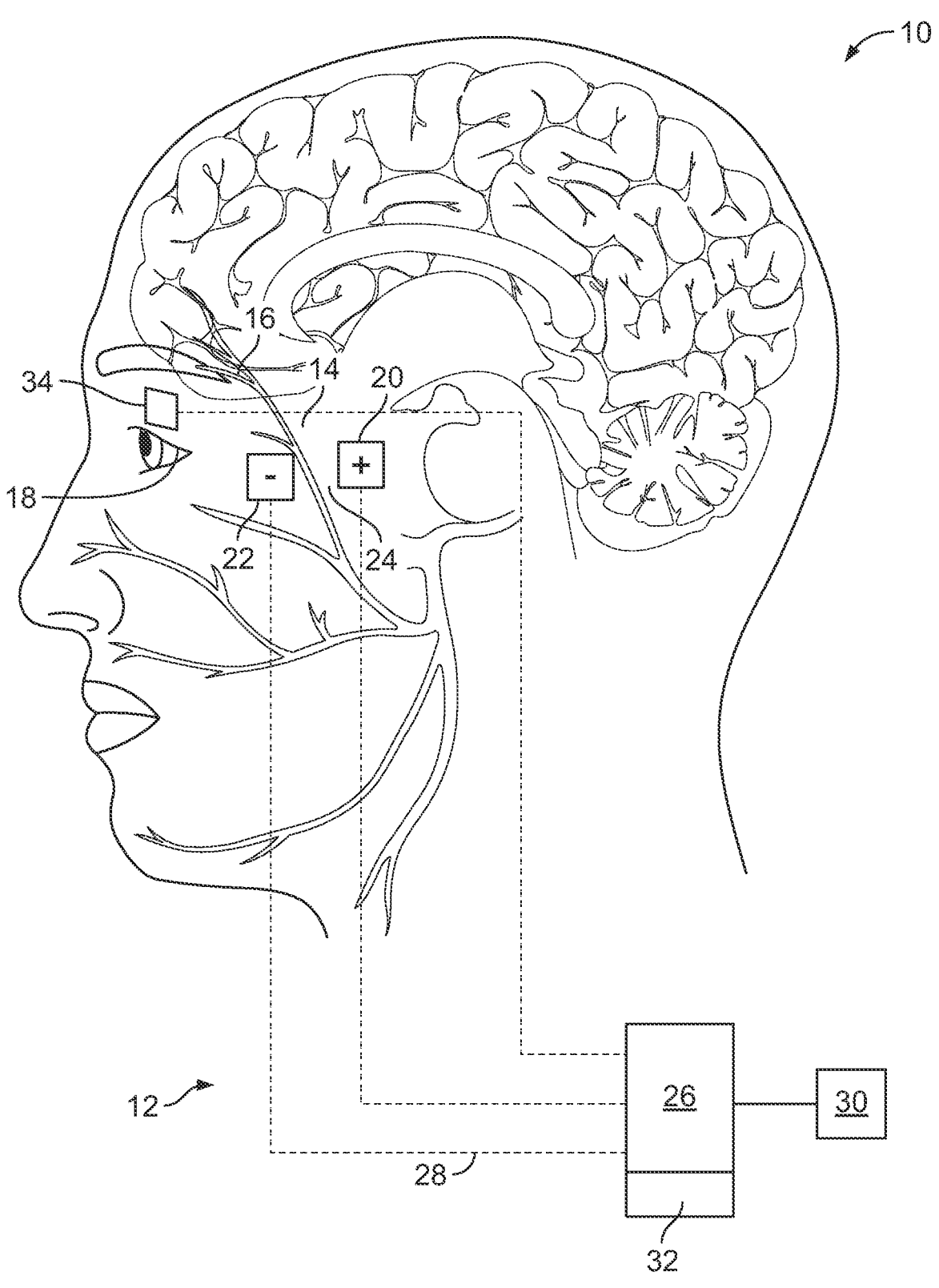
FIG. 1 is a left side view of a patient illustrating the left facial nerve and an example device according to the invention.
Figure 3:
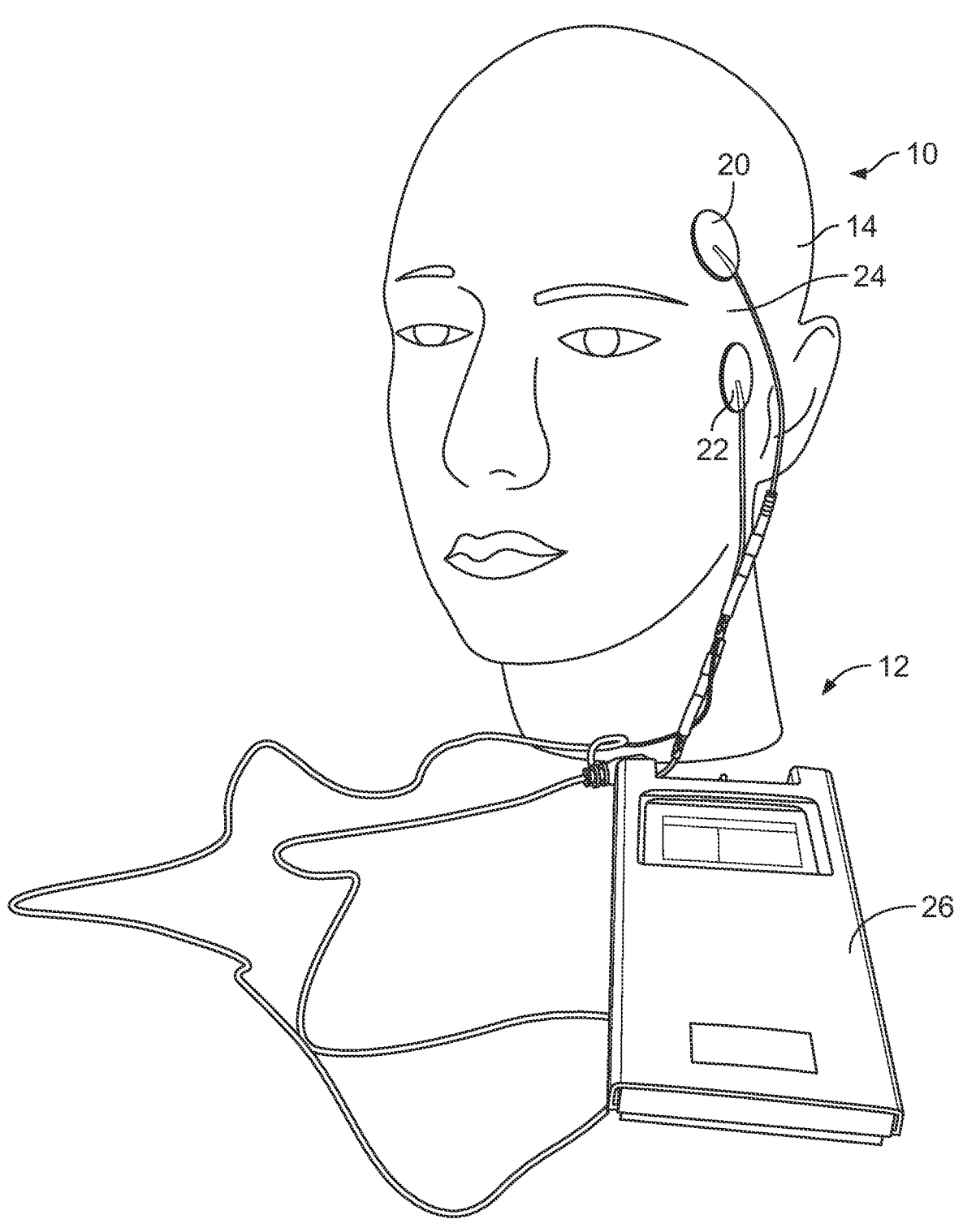
FIG. 3 is a photograph of a prototype of an example device according to the invention.

The invention concerns a device and a method for stimulating left and right eyelid closure of a patient. FIGS. 1 and 3 show a patient 10 using an example embodiment of such a device 12. In this example device 12 comprises a first pair of electrodes 14 configured to be attached proximate to a left facial nerve 16 of the patient for activating closure of the left eyelid 18. Electrodes 14 are positioned in spaced relation to one another, and in this example the electrodes comprise electrode pads 20 and 22 configured to be attached transcutaneously on the left temple 24 of the patient 10. One of the electrode pads, 20, configured to have a positive electrical charge, is configured to be positioned on one side of the facial nerve 16, and the other one of the electrode pads, 22, configured to have a negative electrical charge, is configured to be positioned on an opposite side of the facial nerve.

Device 12 further comprises a second pair of electrodes (not shown), configured to be attached proximate to a right facial nerve of the patient for activating closure of the right eyelid. The second pair of electrodes may be positioned in spaced apart relation to one another on opposite sides of the right facial nerve similar to electrodes 20 and 22, and may also comprise transcutaneously attached electrode pads configured to have opposite polarities.

Device 12 further comprises a controller 26 in communication with the first and second pairs of electrodes (only 14 shown). Controller 26 is configured to provide electrical signals to the first and second pairs of electrodes for stimulating closure of the left and right eyelids. Communication between the controller 26 and the electrodes 14 is symbolized by broken lines 28, and may be effected by wire conductors (see FIG. 3) as well as wirelessly by radio frequency communication devices. Device 12 further comprises a power supply 30 in communication with the controller 26, the power supply configured to supply electrical power to the controller and the first and second pairs of electrodes.

In an example method of operation according to the invention to treat neurotrophic keratitis, the controller 26 is configured to provide the electrical signals to the first and second electrode pairs to stimulate tonic eyelid closure of the right and left eyelids. In another example method of operation the controller is configured provide the electrical signals to the first and second electrode pairs stimulating blinking of the right and left eyelids to treat neurological conditions that result in decrease in the blink rate and blink amplitude such as Parkinson's disease and Progressive Supranuclear Palsy. In this example method the controller is configured to provide the electrical signals to the first and second electrode pairs to control a rate of blink of the right and left eyelids as well as to control a degree of closure of the right and left eyelids.

In an example embodiment, the controller may comprise a driver 32 configured to produce the electrical signals comprising a periodic waveform from 0.001 Hz to 1 Hz. The periodic waveform may comprise a square wave for example. In a practical design, the driver 32 may be configured to produce the electrical signals comprising a current from 5 mA Hz to 100 mA.

Controller 26 may be configured to provide the electrical signals to stimulate closure of one of the eyelids at a time (unilateral operation) or to stimulate closure of both of the eyelids at a time (bilateral operation).

An IRB-approved pilot study examining the range of voltage and current parameters necessary to induce tonic eyelid closure in normal subjects was conducted. This study is being done using an electromyography unit routinely used for muscular stimulation. Placement of the stimulation device over frontal branch of cranial nerve 7 produces an ipsilateral blink or a tonic lid closure movement depending on the stimulation parameters. Preliminary data from the study indicates that a high-frequency low-voltage stimulation is able to produce lid closure. We have studied 10 volunteers, and have successfully induced blink and lid closure in all. Comfort was greatest with stimulation frontal branch of the nerve with a mean discomfort of 1.8±0.7 on a 10-point Likert scale. Electrical current requirements are low, with an average of 25.3±8.7 mA, delivered over an interval of 0.1 s.

As shown in FIG. 1, device 12 may further comprise a first neural blockade electrode 34 configured to be transcutaneously attached to the left eyelid, and a second neural blockade electrode (not shown) configured to be transcutaneously attached to the right eyelid. When transcutaneous neural blockade electrodes 34 are used, the controller is configured to provide blocking electrical signals to the first and second neural blockade electrodes to block left and right branches of the patient's oculomotor nerves to facilitate closure of the eyelids 18. The blocking electrical signals may comprise a kilohertz frequency alternating electrical current. In another example embodiment, shown in FIG. 2, neural blockade electrodes 36 (right electrode shown) may be configured to be subcutaneously implanted around a superior branch of a left oculomotor nerve of the patient, again with the goal of providing blocking left and right branches of the patient's oculomotor nerves to facilitate closure of the eyelids (right eyelid 44 shown). The blocking electrical signals may again comprise a kilohertz frequency alternating electrical current for the example subcutaneous embodiment.

Figure 2:
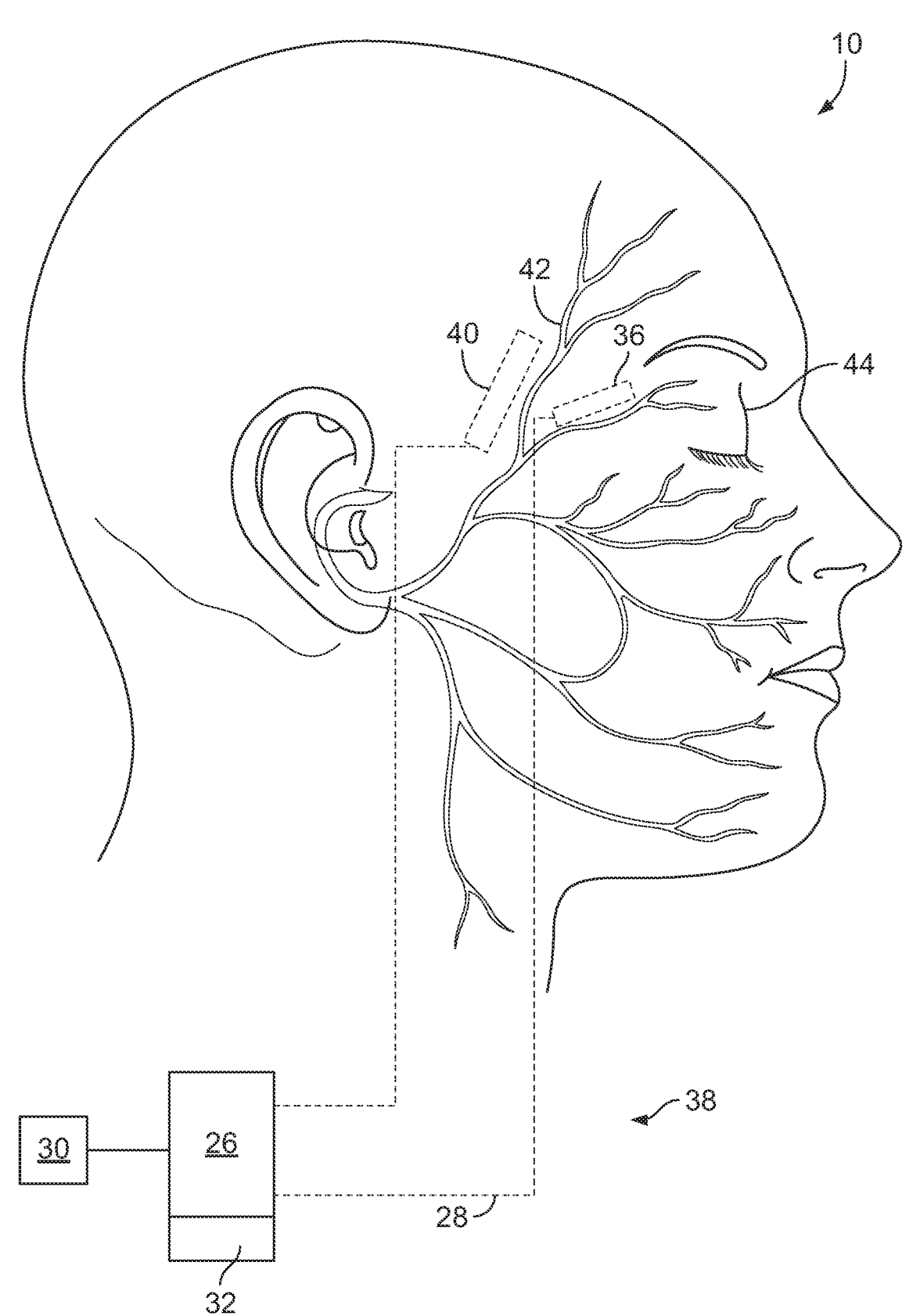
FIG. 2 is a right side view of a patient illustrating the right facial nerve and another example device according to the invention.

FIG. 2 shows a further example embodiment of a device for stimulating left and right eyelid closure of a patient 10. In this example embodiment the device 38 comprises a first bipolar electrode 40 configured to be subcutaneously implanted proximate to a right facial nerve 42 of the patient 10 for activating closure of the right eyelid 44, and a second bipolar electrode (not shown) configured to be subcutaneously implanted proximate to a left facial nerve of the patient for activating closure of the left eyelid. Embodiment 38 may use the same controller 26 in communication with the first and second bipolar electrodes. The controller 26 may comprise the driver 32 and power supply 30 and have the same performance parameters as described above, configured to provide electrical signals to the first and second bipolar electrodes for stimulating closure of the left and right eyelids. Similarly to example embodiment 12, the device embodiment 38 may also be used to treat neurotrophic keratitis via tonic eyelid closure as well as neurological conditions that result in decrease in the blink rate and blink amplitude such as Parkinson's disease and Progressive Supranuclear Palsy.

What is claimed is:

1. A device for stimulating left and right eyelid closure of a patient, said device comprising:
   a first pair of electrodes configured to be attached in spaced apart relation to one another proximate to a left facial nerve of said patient for activating closure of said left eyelid;
   a second pair of electrodes configured to be attached in spaced apart relation to one another proximate to a right facial nerve of said patient for activating closure of said right eyelid;
   a controller in communication with said first and second pairs of electrodes, said controller configured to provide electrical signals to said first and second pairs of electrodes for stimulating closure of said left and right eyelids, wherein said controller is configured provide said electrical signals to said first and second electrode pairs stimulating blinking of said right and left eyelids; and
   a power supply in communication with said controller, said power supply configured to supply electrical power to said controller and said first and second pairs of electrodes.

2. The device according to claim 1, wherein said controller comprises a driver configured to produce said electrical signals comprising a periodic waveform from 0.001 Hz to 1 Hz.

3. The device according to claim 1, wherein said controller comprises a driver configured to produce said electrical signals comprising a current from 5 mA Hz to 100 mA.

4. The device according to claim 1, wherein said first and second electrode pairs comprise first and second pairs of electrode pads configured to be respectively attached transcutaneously on left and right temples of said patient.

5. The device according to claim 4, wherein, for each said pair of electrode pads, one of said electrode pads, configured to have a positive electrical charge, is configured to be positioned on one side of said facial nerve, and another one of said electrode pads, configured to have a negative electrical charge, is configured to be positioned on an opposite side of said facial nerve.

6. The device according to claim 1, wherein said controller is configured to provide said electrical signals to stimulate closure of one of said eyelids at a time.

7. The device according to claim 1, wherein said controller is configured to provide said electrical signals to stimulate closure of both of said eyelids at a time.

8. The device according to claim 1, further comprising:
   a first neural blockade electrode configured to be transcutaneously attached to said left eyelid;
   a second neural blockade electrode configured to be transcutaneously attached to said right eyelid; wherein said controller is configured to provide blocking electrical signals to said first and second neural blockade electrodes to block left and right branches of said patient's oculomotor nerves to facilitate closure of said eyelids.

9. The device according to claim 1, further comprising:
   a first neural blockade electrode configured to be subcutaneously implanted around a superior branch of a left oculomotor nerve of said patient;
   a second neural blockade electrode configured to be subcutaneously implanted around a superior branch of a right oculomotor nerve of said patient; wherein said controller is configured to provide blocking electrical signals to said first and second neural blockade electrodes to block left and right branches of said patient's oculomotor nerves to facilitate closure of said eyelids.

10. A device for stimulating left and right eyelid closure of a patient, said device comprising:

a first bipolar electrode configured to be subcutaneously implanted proximate to a left facial nerve of said patient for activating closure of said left eyelid;

a second bipolar electrode configured to be subcutaneously implanted proximate to a right facial nerve of said patient for activating closure of said right eyelid;

a controller in communication with said first and second bipolar electrodes, said controller configured to provide electrical signals to said first and second bipolar electrodes for stimulating closure of said left and right eyelids, wherein said controller is configured to provide said electrical signals to said first and second bipolar electrodes stimulating blinking of said right and left eyelids; and a power supply in communication with said controller, said power supply configured to supply electrical power to said controller and said first and second bipolar electrodes.

11. The device according to claim 10, wherein said controller comprises a driver configured to produce said electrical signals comprising a periodic waveform from 0.001 Hz to 1 Hz.

12. The device according to claim 10, wherein said controller comprises a driver configured to produce said electrical signals comprising a current from 5 mA Hz to 100 mA.

13. The device according to claim 10, wherein said first and second bipolar electrodes are configured to be implanted along respective frontal branches of said left and right facial nerves.

14. The device according to claim 10, wherein at least one of said controller or said power supply is configured to be subcutaneously implanted within said patient.

15. The device according to claim 10, wherein said controller is configured to provide said electrical signals to stimulate closure of one of said eyelids at a time.

16. The device according to claim 10, wherein said controller is configured to provide said electrical signals to stimulate closure of both of said eyelids at a time.

17. The device according to claim 10, further comprising:

a first neural blockade electrode configured to be attached to said left eyelid;

a second neural blockade electrode configured to be attached to said right eyelid; wherein said controller is configured to provide blocking electrical signals to said first and second neural blockade electrodes to block left and right branches of said patient's oculomotor nerves to facilitate closure of said eyelids.

18. The device according to claim 10, further comprising:

a first neural blockade electrode configured to be subcutaneously implanted around a superior branch of a left oculomotor nerve of said patient;

a second neural blockade electrode configured to be subcutaneously implanted around a superior branch of a right oculomotor nerve of said patient; wherein said controller is configured to provide blocking electrical signals to said first and second neural blockade electrodes to block left and right branches of said patient's oculomotor nerves to facilitate closure of said eyelids.

19. A device for stimulating left and right eyelid closure of a patient, said device comprising:

a first pair of electrodes configured to be attached in spaced apart relation to one another proximate to a left facial nerve of said patient for activating closure of said left eyelid;

a second pair of electrodes configured to be attached in spaced apart relation to one another proximate to a right facial nerve of said patient for activating closure of said right eyelid, wherein said first and second electrode pairs comprise first and second pairs of electrode pads configured to be respectively attached transcutaneously on left and right temples of said patient;

a controller in communication with said first and second pairs of electrodes, said controller configured to provide electrical signals to said first and second pairs of electrodes for stimulating closure of said left and right eyelids; and a power supply in communication with said controller, said power supply configured to supply electrical power to said controller and said first and second pairs of electrodes.

* * * * *